United States Patent [19]

Porat et al.

[11] Patent Number: 5,019,091

[45] Date of Patent: May 28, 1991

[54] FORCEPS

[76] Inventors: Michael Porat, P.O. Box 50355, Tel Aviv, Israel; Amir Porat, 18 Highland Dr., North Caldwell, N.J.

[21] Appl. No.: 160,340

[22] Filed: Feb. 25, 1988

[30] Foreign Application Priority Data

Mar. 23, 1987 [IL] Israel .......................................... 81961

[51] Int. Cl.[5] .............................................. A61B 17/28
[52] U.S. Cl. ...................................... 606/205; 606/210
[58] Field of Search ........................ 128/321, 346, 354; 294/99.2; 606/205–210

[56] References Cited

U.S. PATENT DOCUMENTS

| 3,140,715 | 7/1964 | Whitton, Jr. et al. | 128/321 |
| 3,392,727 | 7/1968 | Hanlon | 128/354 |
| 4,044,771 | 8/1977 | Wannag | 128/354 |
| 4,212,303 | 7/1980 | Nolan | 128/346 |

Primary Examiner—C. Fred Rosenbaum
Assistant Examiner—William W. Lewis
Attorney, Agent, or Firm—Dennison, Meserole, Pollack & Scheiner

[57] ABSTRACT

A method for making molded plastic forceps comprising two opposing elongate arms joined together at one end thereof including the steps of assembling a three-part mold consisting of a first part substantially in the plane of the first arm of the forceps, a second part substantially in the plane of the second arm of the forceps, and a third part between the two arms and defining thereon the construction of the inner surface of the forceps, for example, on one side thereof a mold for a male engagement element and on the other side thereof a mold for a non-apertured female engagement element, injecting a plastics material into the mold, waiting until the plastics material has cooled and contracted, opening the mold by moving first the first part and then the third part, whereby the forceps remains in engagement with the third part, and removing the forceps from the third part by pressing the inside of the joined end away from the mold. The invention also relates to forceps made by this method.

8 Claims, 3 Drawing Sheets

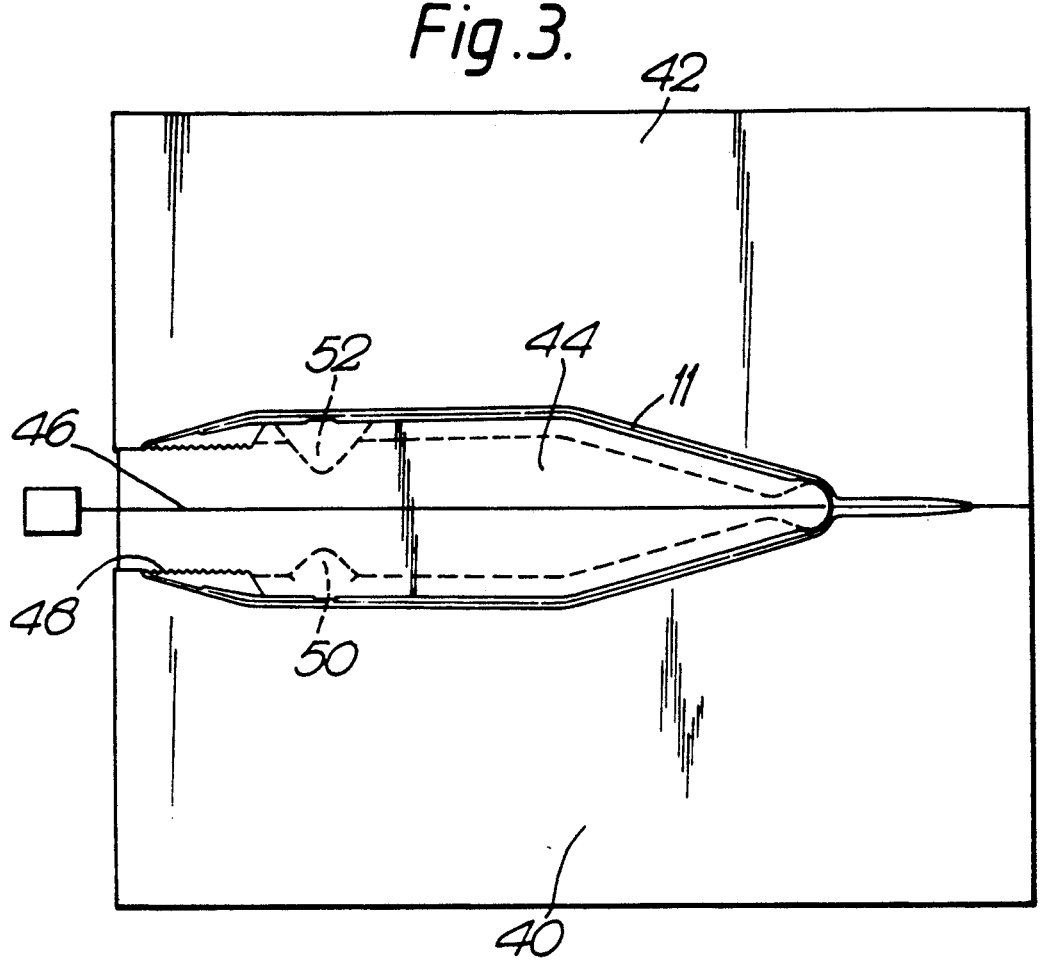
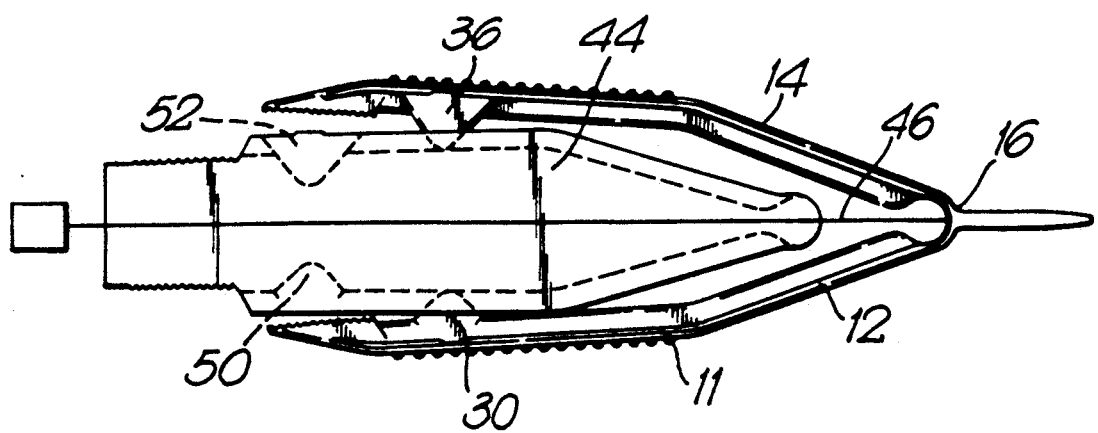

FORCEPS

FIELD OF THE INVENTION

The present invention relates to forceps and tweezers in general and, in particular, to a molded plastics forceps and method for producing it.

BACKGROUND OF THE INVENTION

Forceps and tweezers have long been in use in the medical profession and known in the patent literature. With the advent of plastics materials and methods of injection molding, disposable forceps of molded plastics became common. Such forceps generally comprise a unitary element defining a pair of substantially rigid arms, each terminating in a jaw, connected at the end remote from the jaw by a resilient hinge member which serves to space the arms apart by about 15 degrees and acts as a fulcrum about which the arms can rotate. Compression of the arms causes the jaws to come together in order to grip an object and, on release of the compression forces, the resilience of the hinge member causes the jaws to open.

The jaws of the forceps generally define transversely extending teeth which are staggered so that intermeshing occurs when the jaws are brought together. The intermeshing first occurs at the extreme tips of the jaws and then, as continued force is applied, the teeth are brought into intermeshing relationship over the entire opposing surfaces of the jaws. However, because of the inherent resiliency of plastic suitable for making forceps, in use, the arms of many conventional forceps move laterally relative to one another, thereby reducing the effectiveness of gripping by the tool.

To overcome this problem, special aligning devices and jaw configurations were devised to assure positive mating of the article-gripping surfaces One such means comprises two pairs of opposed lugs on the arms which interengage in use, and is shown in U.S. Pat. No. 3,653,389 (Shannon). Another structure is shown in U.S. Pat. No. 3,906,957 (Weston) including a flexible connector attached between the forceps arms adjacent to the jaws.

Yet another alignment means consists of a pin on one arm adjacent the jaws and a socket in registration therewith on the other arm, as shown, for example, in U.S. Pat. Nos. 3,140,715 (Whitton), 3,265,068 (Holohan) and 3,367,336 (Eizenberg). However, providing such pin and socket elements creates a technical molding problem. Forceps are generally manufactured in a two part mold, the parts being perpendicular to the planes of the arms. After molding, one part is pulled away from the second in order to release the injection molded product which retains a parting line at the intersection of the two parts.

In order to provide apertures in the transverse direction, such as the sockets, a cam-actuated side core is required which moves in and out of engagement with the forceps in the mold. One such side core is required for each aperture in the finished product. Furthermore, since a side core moving in and out of engagement with the forceps in the mold is required for each forceps being produced, only four such forceps can be produced simultaneously. In addition, such molds, aside from being of higher initial cost, are operated with higher maintenance cost. Therefore, forceps of this design are relatively costly and complicated to produce.

Forceps having a pin and a non-apertured female engagement element were not contemplated using conventional molding techniques since they cannot be provided by conventional molds. A non-apertured recess extending at 90 degrees to the forceps arm cannot be generated by a side core because there is no room to remove the side core therefrom.

One method of overcoming this molding problem is described in U.S. Pat. No. 3,392,727 (Hanlon). Hanlon provides a forceps having a flexible connecting hinge which permits one of the arms to move with respect to the other through an angle of about 165 degrees. Thus, the forceps can be molded in a conventional two-part mold in a flat, outstretched orientation and later folded angularly about the connecting hinge into the operating orientation having an angle of about 15 degrees between the arms in the unflexed state. However, this method limits the type of plastic material from which the forceps can be made since not all plastics are bendable.

SUMMARY OF THE INVENTION

It is an object of the present invention to provide forceps and tweezers and a method of making them which simplifies the molding process, lowers the manufacturing cost, and permits the inexpensive production of mating male and female engagement elements.

There is thus provided in accordance with the present invention a method for making molded plastic forceps comprising two opposing elongate arms joined together at one end thereof including the steps of assembling a three-part mold consisting of a first part substantially in the plane of the first arm of the forceps, a second part substantially in the plane of the second arm of the forceps, and a third part between the two arms and defining thereon the construction of the inner surface of the forceps, for example, on one side thereof a mold for a male engagement element and on the other side thereof a mold for a non-apertured female engagement element, injecting a plastics material into the mold, waiting until the plastics material has cooled and contracted, opening the mold by moving first the first part and then the third part, whereby the forceps remains in engagement with the third part, and removing the forceps from the third part by pressing the inside of the joined end away from the mold.

According to a preferred embodiment, the step of removing the forceps includes the step of causing the male and female engagement elements to slide along the sides of the third part during the step of pressing.

There is also provided in accordance with the present invention plastic forceps including two opposing elongate arms of molded plastics joined together at one end thereof and having jaws defining gripping surfaces at the other end thereof, one of said arms defining a male engagement element and the other of said arms defining a complementary non-apertured female engagement element in registration with the male element.

According to a preferred embodiment, the female engagement element includes a pair of protrusions extending perpendicular to the plane of the one arm and the male engagement element includes a complementary protrusion extending perpendicular to the plane of the other arm and disposed in registration with the depression between the protrusions on the female engagement element, the protrusions extending transversely substantially beyond the gripping surfaces of the forceps.

There is further provided in accordance with the present invention a mold for making plastic forceps or tweezers comprising two opposing elongate arms joined together at one end thereof and defining gripping surfaces on the other end thereof including a first part substantially in the plane of the first arm of the forceps, a second part substantially in the plane of the second arm of the forceps, a third part disposed between the two arms and defining the construction of the inner surface of the forceps, and retractable means disposed within the third part for ejecting the forceps from the mold.

BRIEF DESCRIPTION OF THE DRAWINGS

The present invention will be further understood and appreciated from the following detailed description taken in conjunction with the drawings in which:

FIG. 3 is a schematic plan view of a mold constructed and operative in accordance with the present invention in the closed orientation;

FIG. 5 is a schematic detail view of part of the mold of FIG. 3 in the open orientation.

DETAILED DESCRIPTION OF THE INVENTION

Figure 1:
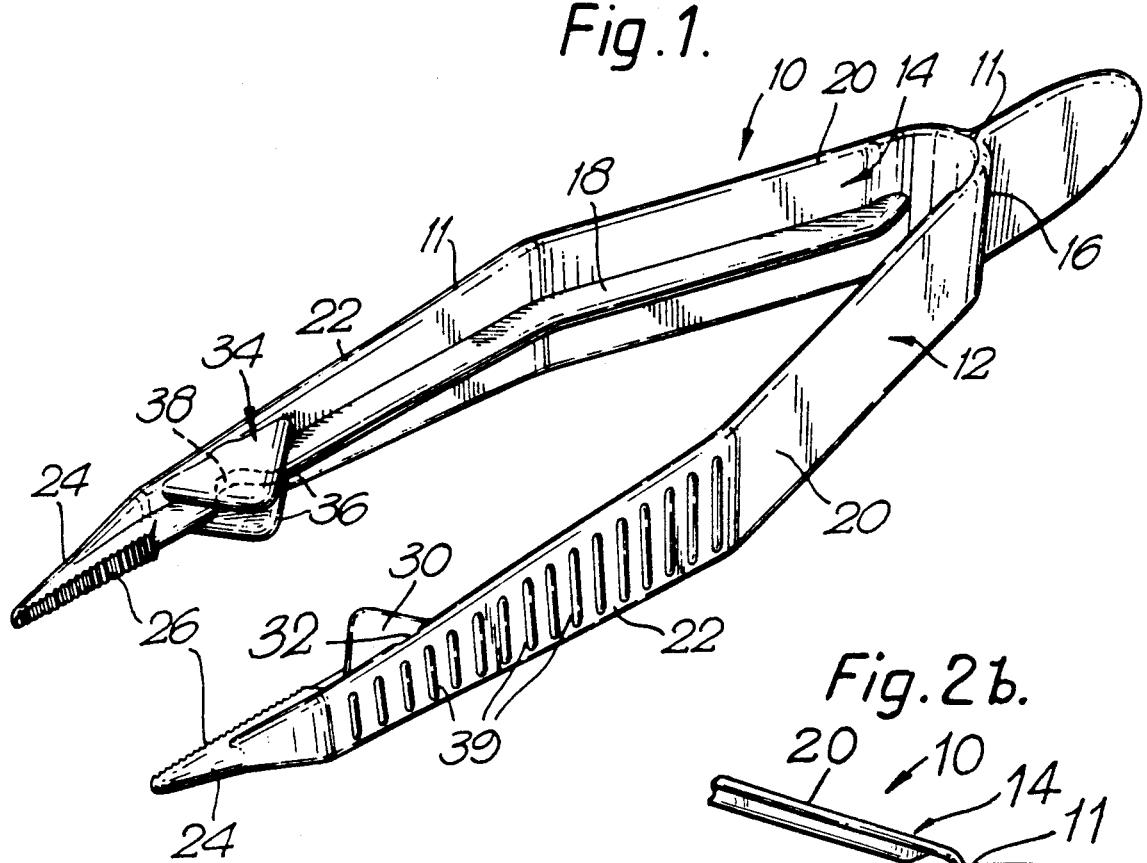
FIG. 1 is a perspective view of forceps constructed and operative in accordance with the present invention.
Figure 2B:
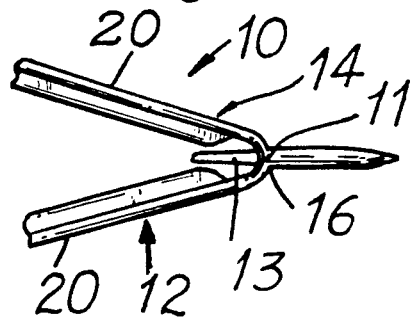
FIG. 2b is a partial side view of the forceps illustrating a further embodiment with an optional tongue.
Figure 2A:
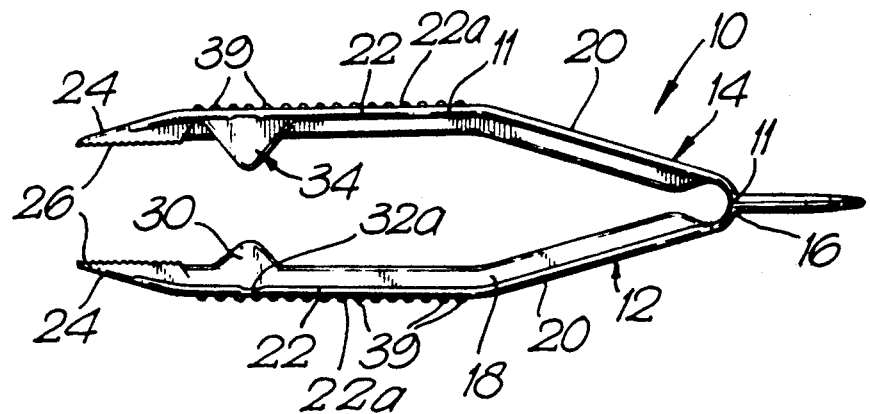
FIG. 2a is a side view of the forceps of FIG. 1.

Referring now to FIGS. 1 and 2a there are shown respective perspective and side views of forceps constructed and operative in accordance with the present invention and generally indicated as 10. Forceps 10 comprise a unitary molded plastic tool having a parting line 11 and including two arms 12 and 14 joined together by a flexible hinge 16, as known. It is a particular feature of the present invention that parting line 11 is defined on the side edges of the arms 12 and 14, and not on the outside surface thereof, as is usually the case in existing forceps.

Arms 12 and 14 are generally T-shaped in crosssection, having longitudinal ribs 18 extending centrally along their inner opposing surfaces to strengthen the arms. The inner portion of each rib 18 adjacent hinge 16 tapers rearwardly. Noting FIG. 2b in particular, an optional tongue 13 may be provided affixed to hinge 16 and extending between arms 12 and 14 beyond the tapering portion of ribs 18.

Arms 12 and 14 define three sections. The first sections 20 of the arms extend at an angle from hinge 16 away from each other and merge into the second sections 22 which are substantially parallel to one another. The outer ends of arms 12 and 14 define jaws 24 including gripping surfaces 26 which comprise a plurality of transverse teeth. Preferably, the teeth comprise male and female mating elements, i.e., the teeth on one jaw mesh into the spaces between the teeth on the other jaw, and vice versa. Ribs 18 extend substantially the full length of the arms between the jaws and the connecting hinge, the gripping surfaces 26 being defined on portions of the arms which merge into the ribs.

Arms 12 and 14 are provided with mating alignment means adjacent jaws 24. Arm 12 defines a single male protrusion 30 extending from rib 18 perpendicular to the plane of arm 12. Two recesses 32 are provided on either side of protrusion 30 in arm 12.

Arm 14 defines a non-apertured female mating element 34 comprising a pair of parallel protrusions 36 extending from and perpendicular to arm 14 on either side of rib 18 and extending substantially therebeyond. The tips of protrusions 36 are in registration with recesses 32 on arm 12. A recess 38 is defined in rib 18 on arm 14 between protrusions 36 and in registration with the tip of protrusion 30.

Protrusions 30 and 36 are configured for tight sliding engagement whereby substantially no lateral movement of arm 12 relative to arm 14 is permitted. Furthermore, protrusions 30 and 36 and recesses 32 and 38 act as stop means to limit the pressure the teeth on gripping surface 26 exert on each other and also to insure complete engagement therealong.

Preferably, protrusions 30 and 36 have sloping sides. This permits the protrusions to slide out of the mold in which the forceps are formed and to slide down the sides thereof.

It is a particular feature of the present invention that protrusions 30 and 36 act together with ribs 18 to strengthen arms 12 and 14. Thus, neither recesses 32 nor recess 38 detract from the strength of the forceps in use, as can occur in conventional forceps.

Transverse ribs 39 may be provided on the second sections 22 of arms 12 and 14 to provide a good grip by the user, as known.

Operation of the forceps of the present invention is as follows. When it is desired to grip an object, pressure is exerted on second sections 22 squeezing arms 12 and 14 towards one another. Before the gripping teeth 26 begin to mesh, protrusion 30 enters between protrusions 36 preventing lateral movement between the two arms. As more pressure is applied, the gripping teeth begin to mesh, beginning from the outer tip of jaws 24 and progressing inwardly therealong until all the teeth mesh.

If excess pressure is applied at 22a, protrusion 30 will seat in recess 38 and protrusions 36 seat in recesses 32, causing protrusions 36 to act as a pivot at 32a. As the arms pivot about 32a, jaws 24 are forced to open, which is undesirable. Further application of pressure may cause the forceps to break. Again noting FIG. 2b in particular, the tongue 13 may optionally be provided to prevent pivoting about the protrusions at 32a and to prevent breakage when excess pressure is applied.

Figure 4:
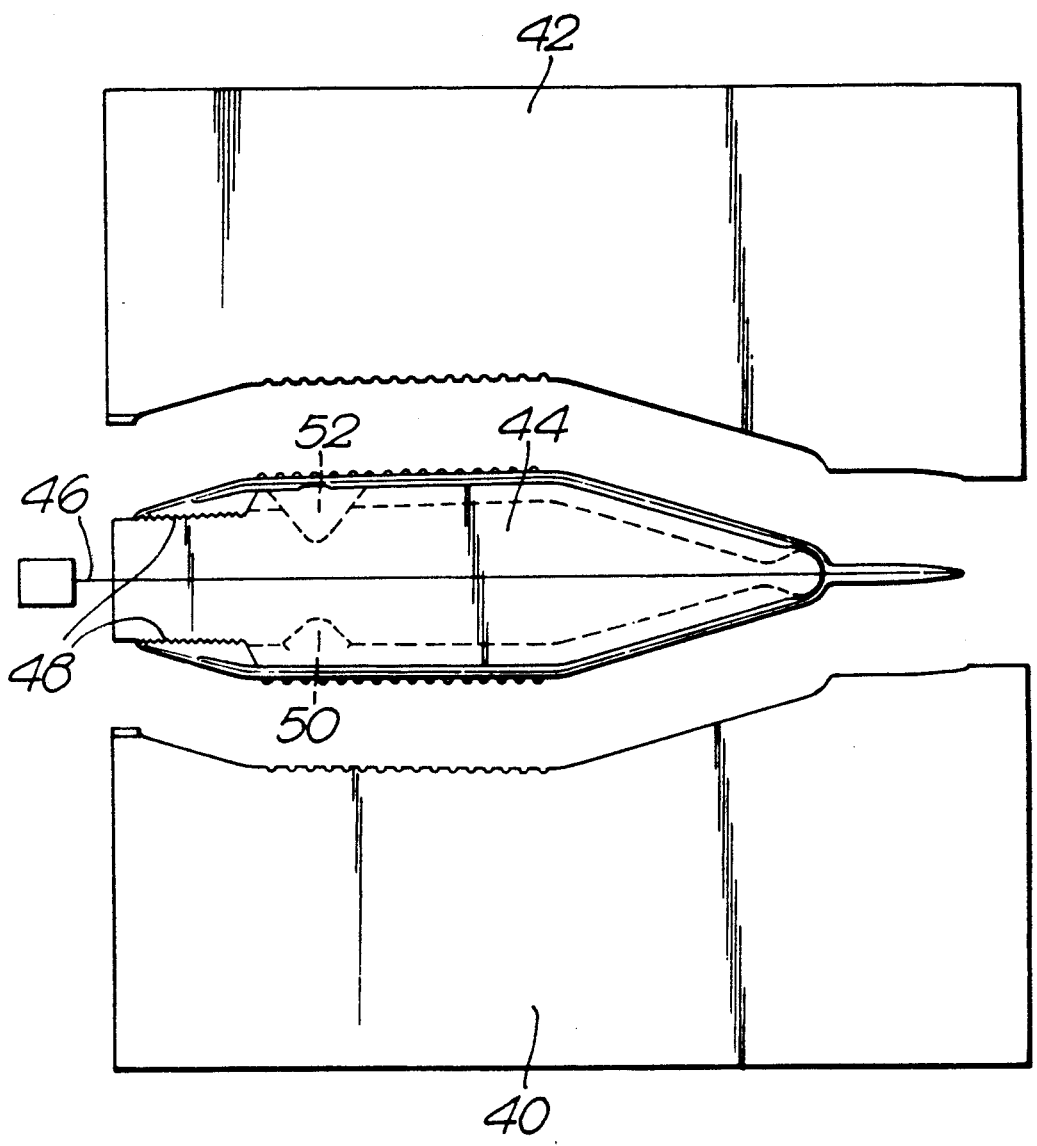
FIG. 4 is a schematic plan view of the mold of FIG. 3 in the open orientation.

Referring now to FIGS. 3, 4 and 5 there is shown a schematic plan view of a mold for a forceps constructed and operative in accordance with the present invention in respective closed and open orientations. The mold comprises a first portion or side core 40 affixed to the injection molding apparatus (not shown) and extending in a plane perpendicular to the plane of arm 12, a second portion or side core 42, extending in a plane perpendicular to the plane of arm 14, and a third portion or central core 44 disposed between arms 12 and 14.

Retractable ejection means 46, such as a piston, is provided disposed in the third portion 44. Ejection means 46 is operative to press against the inner surface of hinge portion 16 of the molded forceps. The surface of third portion 44 defines the construction of the inner surface of the forceps, including grooves for forming ribs 18, recesses 48 which will define the gripping teeth 26 of the forceps and larger recesses 50 and 52 which will define protrusions 30 and 36.

The method of producing forceps utilizing this mold is as follows. The mold is assembled in the closed orientation of FIG. 3 and the plastics material is injected as known per se. When it is desired to remove the molded forceps, the mold is opened, as shown in FIG. 4, by moving the second portion 42 and third portion 44 away from the first portion 40. As illustrated, the forceps remains seated on third portion 44.

Due to the natural shrinkage of the plastic as it solidifies from the fluid state (from about 0.5% and higher, depending on the particular plastic material), the gripping teeth disengage from recesses 48 as the plastic cools. Ejection means 46 is then actuated and presses the hinge 16 of the forceps in the downward direction, as shown in FIG. 5. Due to the angled lower edge of protrusions 30 and 36, the protrusions slide out of recesses 50 and 52 and along the outer surface of third portion 44, causing the forceps to open wider than the normal operating distance. Since the protrusions extend substantially beyond gripping teeth 26, teeth 26 do not come in contact with the edges of the mold during ejection.

It is a particular feature of the present invention that the forceps are removed from the mold substantially without damaging the gripping teeth. This is due to the shrinkage of the plastic upon cooling and the opening of the forceps due to pressure of protrusions 30 and 36 on the surface of the mold.

While the mold has been described hereinabove with reference to one forceps, it will be appreciated that a plurality of forceps can be molded simultaneously. In this case, a plurality of cavities adjacent one another along the length of the mold are provided, one for each forceps, one ejection means being associated with each cavity. Thus, any desired number of forceps can be molded simultaneously, depending only upon the desired length of the mold.

It will be appreciated by those skilled in the art that the invention is not limited to what has been shown and described hereinabove by way of example. Rather, the scope of the invention is limited solely by the claims that follow.

We claim:

1. Plastic forceps comprising:
   two opposing elongate arms of molded plastics having first ends joined together by an integral hinge, having second ends with jaws defining gripping surfaces at said second ends, and having inner opposing surfaces;
   said hinge maintaining said arms in spaced overlying relation to each other for limiting outward movement of said arms relative to each other and for selective movement of said arms and gripping surfaces toward each other;
   longitudinal ribs extending centrally along said inner opposing surfaces of said arms;
   means for preventing lateral movement of said arms during gripping including a male engagement element defined on one of said arms and a complementary female engagement element defined on the other of said arms and disposed in registration with said male element;
   said female engagement element includes a closed inner end and comprises a pair of laterally aligned protrusions extending perpendicular to the inner surface of said other of said arms on either side of the rib thereon;
   said male engagement element comprises a complementary protrusion extending from the rib on said one of said arms perpendicular to the inner surface of the arm and disposed in registration between the protrusions on the female engagement element;
   said protrusions extending substantially beyond the ribs and the gripping surfaces of the forceps; and
   said closed inner end of said female engagement element comprises a recess in said rib between said pair of protrusions of the female engagement element for selective reception of the protrusion of the male engagement element upon movement of the arms toward each other.

2. Plastic forceps according to claim 1, including a pair of recesses, one positioned in the corresponding arm on each side of said protrusion of the male engagement element for selective reception of the pair of protrusions of the female engagement element upon movement of the arms toward each other.

3. Plastic forceps according to claim 2 wherein said protrusions of said male and said female engagement elements simultaneously engage in said recesses to limit movement of the arms toward each other and prevent excessive pressure on said gripping surfaces.

4. Plastic forceps according to claim 3 and wherein said protrusions define sloping sides.

5. Plastic forceps according to claim 3 including an elongate tongue having one end fixed to said hinge and extending therefrom between and generally parallel to said arms for limiting movement of said arms toward each other.

6. Plastic forceps comprising:
   two opposing elongate arms of molded plastics having first ends joined together by an integral hinge, having second ends with jaws defining gripping surfaces at said second ends, and having inner opposing surfaces;
   said hinge maintaining said arms in spaced overlying relation to each other for limiting outward movement of said arms relative to each other and for selective movement of said arms and gripping surfaces toward each other;
   longitudinal ribs extending centrally along said inner opposing surfaces of said arms;
   means for preventing lateral movement of said arms during gripping including a male engagement element defined on one of said arms and a complementary female engagement element defined on the other of said arms and disposed in registration with said male element;
   said female engagement element includes a closed inner end and comprises a pair of laterally aligned protrusions extending perpendicular to the inner surface of said other of said arms on either side of the rib thereon;
   said male engagement element comprises a complementary protrusion extending from the rib on said one of said arms perpendicular to the inner surface of the arm and disposed in registration between the protrusions on the female engagement element;
   said protrusions extending substantially beyond the ribs and the gripping surfaces of the forceps; and
   a tongue having one end fixed to said hinge and extending between and generally parallel to said arms.

7. Plastic forceps according to claim 6, wherein said tongue aligns with said ribs whereby said ribs engage said tongue upon movement of said arms toward each other and thereby limit movement of said arms and prevent application of excessive pressure.

8. Plastic forceps comprising:

two opposing elongate arms of molded plastics having first ends joined together by an integral hinge, having second ends with jaws defining gripping surfaces at said second ends, and having inner opposing surfaces;

said hinge maintaining said arms in spaced overlying relation to each other for limiting outward movement of said arms relative to each other and for selective movement of said arms and gripping surfaces toward each other;

longitudinal ribs extending centrally along said inner opposing surfaces of said arms;

means for preventing lateral movement of said arms during gripping including a male engagement element defined on one of said arms and a complementary female engagement element defined on the other of said arms and disposed in registration with said male element;

said female engagement element includes a closed inner end and comprises a tongue having one end fixed to said hinge and extending between and generally parallel to said arms for engagement of the ribs thereagainst to limit movement of the arms toward each other.

* * * * *